US011708760B2

(12) United States Patent
DiFoggio et al.

(10) Patent No.: US 11,708,760 B2
(45) Date of Patent: Jul. 25, 2023

(54) IMMERSED LENS DOWNHOLE REFRACTOMETER (71) Applicant: Baker Hughes Oilfield Operations LLC, Houston, TX (US)

(72) Inventors: Rocco DiFoggio, Houston, TX (US); Helene C. Climent, Houston, TX (US)

(73) Assignee: Baker Hughes Oilfield Operations LLC, Houston, TX (US)

( * ) Notice: Subject to any disclaimer, the term of this patent is extended or adjusted under 35 U.S.C. 154(b) by 239 days.

(21) Appl. No.: 16/815,410

(22) Filed: Mar. 11, 2020

(65) Prior Publication Data
US 2020/0291777 A1 Sep. 17, 2020

Related U.S. Application Data (60) Provisional application No. 62/817,341, filed on Mar. 12, 2019.

(51) Int. Cl.
*G01N 21/43* (2006.01)
*E21B 49/08* (2006.01)
*G01N 33/28* (2006.01)
*G01N 21/41* (2006.01)

(52) U.S. Cl.
CPC .......... *E21B 49/08* (2013.01); *G01N 21/4133* (2013.01); *G01N 21/431* (2013.01); *G01N 33/2823* (2013.01); *G01N 2021/432* (2013.01); *G01N 2201/0833* (2013.01)

(58) Field of Classification Search
CPC . E21B 49/08; E21B 49/0875; G01N 21/4133; G01N 21/431; G01N 33/2823; G01N 2021/432; G01N 2201/0833; G01N 2021/8514
See application file for complete search history.

(56) References Cited

U.S. PATENT DOCUMENTS

| | | | |
|---|---|---|---|
| 4,682,889 A | 7/1987 | Harmer | |
| 5,167,149 A | 12/1992 | Mullins | |
| 5,201,220 A | 4/1993 | Mullins | |
| 5,351,532 A | 10/1994 | Hager | |
| 6,049,088 A * | 4/2000 | Harding | G01F 23/2925 250/577 |
| 6,355,928 B1 | 3/2002 | Skinner | |
| 6,401,529 B1 | 6/2002 | Robison | |
| 7,016,026 B2 | 3/2006 | DiFoggio | |

(Continued)

OTHER PUBLICATIONS

International Search Report and Written Opinion dated Jun. 12, 2020 in corresponding PCT Application No. PCT/US20/22285.

(Continued)

*Primary Examiner* — Hwa Andrew Lee
(74) *Attorney, Agent, or Firm* — Hogan Lovells US LLP (57) ABSTRACT An apparatus for detecting one or more properties of a downhole fluid includes a housing. The apparatus also includes a location-sensitive optical detector, arranged within a chamber formed by the housing. The apparatus further includes a light source, arranged within the chamber. The apparatus also includes a lens, positioned at an end of the housing, the lens preferably having a flat side and a curved side, the flat side positioned proximate the chamber to position the flat side closer to the light source than the curved side. The apparatus further includes a mirror, arranged outside the housing.

5 Claims, 8 Drawing Sheets (56) References Cited

U.S. PATENT DOCUMENTS

| | | | |
|---|---|---|---|
| 7,763,845 B2* | 7/2010 | Estes | E21B 47/024 |
| | | | 250/269.1 |
| 9,599,554 B2 | 3/2017 | Price | |
| 9,690,989 B2 | 6/2017 | Hay | |
| 9,733,182 B2 | 8/2017 | DiFoggio | |
| 2010/0053621 A1 | 3/2010 | Olson | |
| 2010/0252737 A1* | 10/2010 | Fournel | G01J 3/02 |
| | | | 250/338.4 |
| 2011/0108719 A1 | 5/2011 | Ford | |
| 2013/0219997 A1 | 8/2013 | Sullivan | |
| 2014/0060821 A1 | 3/2014 | Rodney | |
| 2014/0300889 A1 | 10/2014 | DiFoggio | |
| 2018/0024052 A1 | 1/2018 | Accetta | |
| 2022/0283081 A1* | 9/2022 | Nagase | G01N 21/61 |

OTHER PUBLICATIONS

P. Y. Liu et al., "An optofluidic imaging to measure the biophysical signature of single waterborne bacterium," Lab on a Chip, Royal Society of Chemistry, Jan. 2013, vol. 1, No. 1, 24 pages.

R. S. Kasana et al., "Refractometry of Liquid by Using Liquid Immersion and Three Beam Interferometric Techniques," International Journal of Pure and Applied Physics, 2010, vol. 6, No. 3, pp. 263-268.

Sastry CBSE, "Important Questions for CBSE Class 12 Physics Reflection, Refraction and Dispersion of Light," Dec. 4, 2015, http://www.learncbse.in/important-questions-for-class-12-physics-cbse-reflection-refraction-and-dispersion-of-light/, 19 pages.

* cited by examiner

IMMERSED LENS DOWNHOLE REFRACTOMETER

CROSS REFERENCE TO RELATED APPLICATIONS

This application claims priority to and the benefit of U.S. Patent Application Ser. No. 62/817,341 filed Mar. 12, 2019 titled "IMMERSED LENS DOWNHOLE REFRACTOMETER," the full disclosure of which is hereby incorporated herein by reference in its entirety for all purposes.

BACKGROUND

1. Field of Disclosure

This disclosure relates in general to oil and gas tools, and in particular, to systems and methods for downhole measurements, such as identification and property measurement of downhole fluids.

2. Description of the Prior Art

In oil and gas production, various measurements may be conducted in downhole environments in order to analyze one or more properties of hydrocarbon formations. One such measurement is an index of refraction of the formation fluids. In formation testing and sampling, knowing the refractive index of a downhole fluid allows one to assess other fluid properties including 1) identify the fluid (oil, water, gas), 2) estimate various properties of the fluid (brine salinity, crude oil density), and 3) monitor sample cleanup progress when attempting to collect a fluid sample. Additionally, the refractive index can be used to monitor both oil-based mud (OBM) filtrate contamination cleanup when collecting a sample of crude oil from the formation and water-based mud (WBM) filtrate contamination cleanup when collecting a sample of formation brine using a formation testing and sampling tool such as a Reservoir Characterization Instrument. In production logging, refractive index can be used to distinguish all three fluid phases (oil, water, gas). However, various commercial downhole refractometers use light reflected at the interface of a downhole fluid with a window and give erroneous readings in multiphase flow when black oil is not quickly or completely flushed from the window surface by passage of a subsequent water or gas phase.

SUMMARY

Applicant recognized the problems noted above herein and conceived and developed embodiments of systems and methods, according to the present disclosure, for determination of downhole formation properties.

In an embodiment, an apparatus for detecting one or more properties of a downhole fluid includes a housing. The apparatus also includes a detector, arranged within a chamber formed by the housing. The apparatus further includes a light source, arranged within the chamber. The apparatus also includes a lens, positioned at an end of the housing, the lens having a flat side and a curved side, the flat side positioned proximate the chamber to position the flat side closer to the light source than the curved side. The apparatus further includes a mirror, arranged outside the housing.

In an embodiment, an apparatus for detecting one or more properties of a downhole fluid includes a housing, a location-sensitive optical detector, arranged within a chamber formed by the housing, and a light source, arranged within the chamber. The apparatus further includes a lens, positioned at an end of the housing and a mirror, arranged outside the housing.

In an embodiment, a system for determining one or more fluid properties includes a tool component adapted to be secured to a tool string for use in a downhole environment and a sensor associated with the tool component. The sensor includes a pressure housing having a chamber, a lens, forming at least a portion of the pressure housing, a detector, arranged within the chamber formed by the housing, a light source, arranged within the chamber, and a mirror positioned outside the housing.

In an embodiment, a method for determining one or more fluid properties in a downhole environment includes emitting a beam, from a light source positioned in a chamber formed in a pressure housing, toward a lens. The method also includes directing, through the lens, the beam toward a mirror, at least a portion of the lens and the mirror being immersed in a fluid. The method further includes receiving, from the mirror and through the lens, a reflected beam at a detector. The method also includes determining, based at least in part on the reflected beam, the one or more fluid properties.

BRIEF DESCRIPTION OF THE DRAWINGS

The present technology will be better understood on reading the following detailed description of non-limiting embodiments thereof, and on examining the accompanying drawings, in which.

DETAILED DESCRIPTION

The foregoing aspects, features and advantages of the present technology will be further appreciated when considered with reference to the following description of preferred embodiments and accompanying drawings, wherein like reference numerals represent like elements. In describing the preferred embodiments of the technology illustrated in the appended drawings, specific terminology will be used for the sake of clarity. The present technology, however, is not intended to be limited to the specific terms used, and it is to be understood that each specific term includes equivalents that operate in a similar manner to accomplish a similar purpose.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of operating parameters and/or environmental conditions are not exclusive of other parameters/conditions of the disclosed embodiments. Additionally, it should be understood that references to "one embodiment", "an embodiment", "certain embodiments," or "other embodiments" of the present disclosure are not intended to be interpreted as excluding the existence of additional embodiments that also incorporate the recited features. Furthermore, reference to terms such as "above," "below," "upper", "lower", "side", "front," "back," or other terms regarding orientation are made with reference to the illustrated embodiments and are not intended to be limiting or exclude other orientations. Moreover, like reference numerals may be used for like items throughout the specification, however, such usage is for convenience and is not intended to limit the scope of the present disclosure.

Currently, commercial downhole refractometers use reflected light at the interface of a downhole fluid with a window either by measuring the fraction of light that is reflected (U.S. Pat. No. 7,016,026) or by measuring the angle at which there is a light-to-dark reflection transition (U.S. Pat. Nos. 5,167,149 and 5,201,220) in a critical angle refractometer.

In another example of existing refractometers described in U.S. Pat. No. 9,733,182, the angle at which light exits a transparent planar solid surface (in a first pressure housing) in combination with a remote detector (in a second pressure housing) is used to measure the fluid's refractive index. Other methods may use a Zeiss immersion refractometer, which do not have a lens or a focal length. U.S. Patent Publication No. 2018/0024052 describes using intensity of light transmitted through solid glass optical fibers that are immersed in a liquid to determine refractive index of that liquid. Embodiments of the present disclosure use no fibers and use an angle of a light beam and not its intensity, which as will be described herein, provides distinct advantages over the existing technologies.

Other methods may be used to measure the refractive index of irregular grains of solids by immersion in a known refractive-index liquid. Furthermore, methods may incorporate slits and interference patterns and using the spacing of the interference fringes. Additionally, methods may include moving parts for adjusting a focal plane or using a refractive index to measure the concentration of solute in a liquid independent of the liquid's temperature.

In other fields, such as optofluidic imaging for microbe evaluation, contrast is observed between bacteria and a mixture of water and Ficoll polysaccharide in which they are immersed. When mixture matches bacteria's refractive index, contrast is eliminated. Moreover, contrast may be observed between microbes and various immersion fluids. Additionally, refractive indexes may be matched to spectra of E. coli.

Reflection methods produce erroneous readings when, over the short path length of the evanescent wave at the window-fluid interface, the fluid (most often, the asphaltenes in a crude oil) significantly absorbs the color (wavelength) of light that is used. Such light absorption can produce too low a reflected light intensity so that the reflected light is no longer simply a function of the refractive index mismatch between fluid and window or it can reduce the contrast so much that a critical angle refractometer's light-to-dark transition angle is not detectable.

In various embodiments of the present disclosure, a curved refractive surface (e.g., a lens), in combination with a mirror, which may also be curved, allows both the light source and detector to be located on the same side of the lens within a single pressure housing, which considerably simplifies the engineering of the refractometer. For simplicity, a plano-convex lens is used with the flat side within the atmospheric pressure housing and the curved side in contact with the high-pressure fluid. However, it should be appreciated that lenses with different shapes may also be utilized in various embodiments. A beam of light that enters perpendicular to the flat side of the lens converges towards a now-longer focal point but the light encounters a mirror first. The reflected light re-enters the lens and emerges out of the plano side of the lens at various angles depending upon the refractive index of the fluid.

This emergent angle can be determined using a photodiode array, Charge-Coupled Device (CCD) array, Position Sensitive Detector (CCD), or other means. For production logging, one can use three bundles of fibers each terminated with a photodiode, where one bundle is placed at an angular region for oil, another for water, and a third for gas. Fluid identification as either oil, water, or gas, may be determined as the "brightest fiber bundle wins." Note that, for a plano-convex lens, one side is flat so it does not bend the light striking it perpendicularly. The other side is curved and leads to the bending of light so, for a plano-convex lens with light entering the plano side at 90 degrees, only the curved side needs to be in contact with the fluid whose refractive index is being measured.

Embodiments of the present disclosure may be used to determine an unknown refractive index of a liquid, as opposed to determining an unknown refractive index of a glass particle that is immersed in a known refractive index liquid, where the particle seems to disappear when the liquid matches its refractive index. Furthermore, embodiments may not include moving parts, slits, or interference patterns.

Embodiments of the present disclosure offer advantages such as an improvement over the glass rod approach of commercial tools because embodiments of the present disclosure include only a single pressure housing for both the light source and detector instead of needing a separate housing for each because light makes a round trip through the lens, which would not be feasible with a glass rod approach. Moreover, the immersed lens approach described herein reads refractive index over a macroscopic path length, which is much greater than any fluid coating thickness so it is not affected by the presence of such coatings or how long it takes to flush them away from the surface. Additionally, the immersed lens approach would give a better and more reliable refractive index reading.

Figure 1:
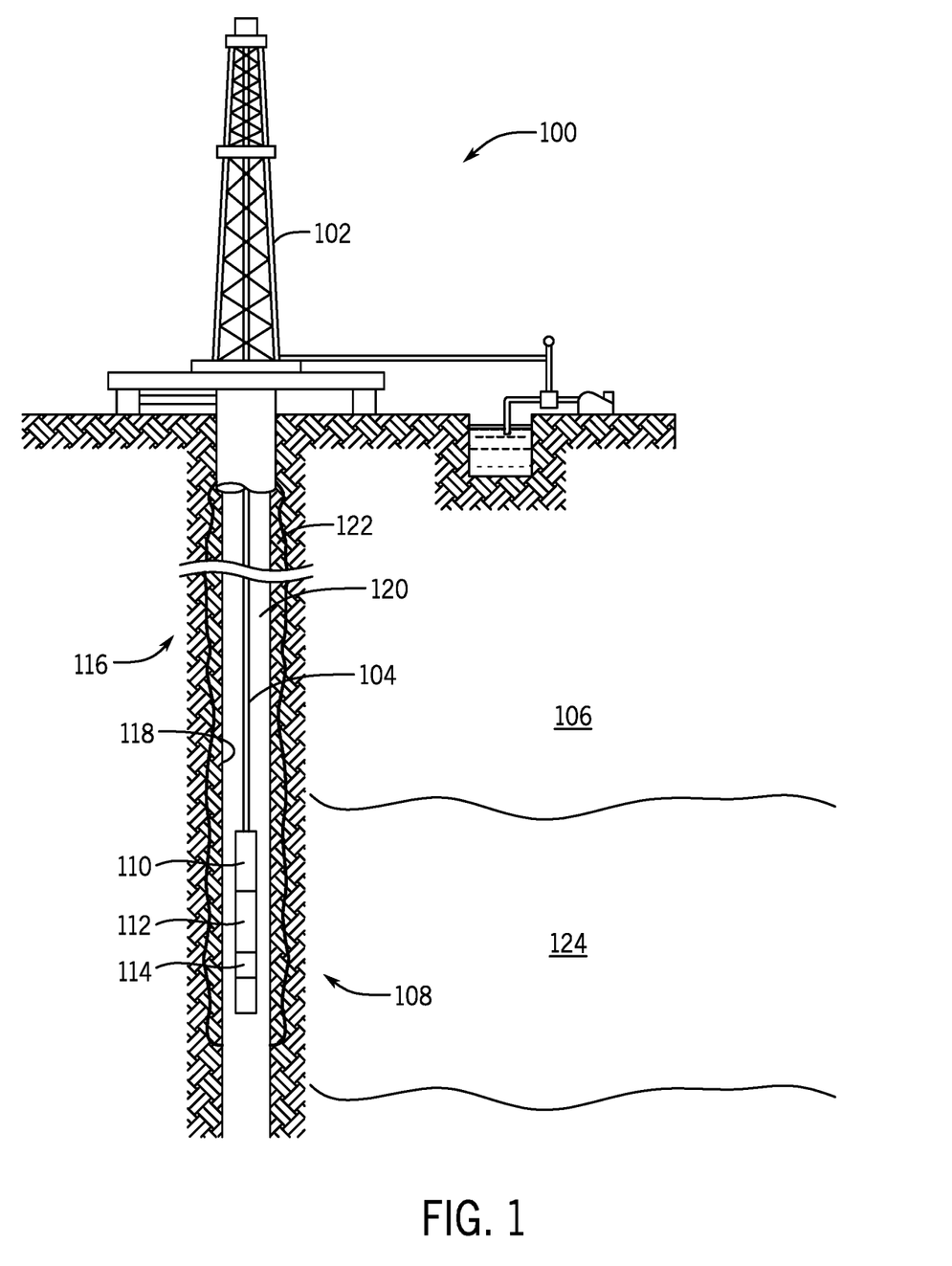
FIG. 1 is a schematic side view of an embodiment of a drilling system, in accordance with embodiments of the present disclosure.

FIG. 1 is a schematic side view of an embodiment of a wellbore system 100 including a rig 102 and a drill string 104 extending into a downhole formation 106. It should be appreciated that while various embodiments may be discussed with reference to the illustrated wellbore system 100, other embodiments may include other wellbore systems that may include wirelines, coiled tubing, and the like. For example, various embodiments of the present disclosure may be incorporated into logging operations, product operations, measurement while drilling operations, and the like.

Accordingly, discussion with reference to drill strings 104 is for illustrative purposes only. The illustrated drill string 104 is formed from a plurality of tubulars joined together, for example via threads, and extends into the formation 106 to a bottom hole assembly (BHA) 108. In the illustrated embodiment, the BHA 108 includes a plurality of segments representative of one or more measurement or operational systems. For example, the BHA 108 may include a refractometer 110, a communication system 112, and a sampling system 114, among other such options. In various embodiments, the BHA 108 may include additional or fewer units, and further, may be utilized to conduct one or more downhole measurement operations. Additionally, it should be appreciated that the drill string 104 may include various other components, which have been removed for simplicity and clarification with the discussion herein. Furthermore, while embodiments may be discussed with reference to drilling operations, in other embodiments the measurements may be conducted during logging periods, intervention periods, and the like.

As illustrated in FIG. 1, in various embodiments a wellbore 116 extends into the formation 106 and includes a borehole sidewall 118 and an annulus 120 arranged between the BHA 108 and the sidewall 118. In certain embodiments, during formation of the wellbore 116, the drill string 104 may include a drill bit that is driven to rotate. In various embodiments, fluid such as drilling mud may be pumped through the drill string 104 and through the drill bit, where the drilling mud may infiltrate the formation 106 in a near-borehole zone 122. Accordingly, as will be described below, measurements obtained from various systems, such as the systems illustrated with the BHA 108, may be inaccurate because of the infiltration.

In various embodiments, the BHA 108 may be utilized to determine the location of a recoverable zone 124 within the formation 106. The recoverable zone 124 may refer to a region of the formation 106 that includes recoverable hydrocarbons. It is desirable for operators to determine the presence of hydrocarbons in this region, among other potential fluids, to inform potential recovery operations. For example, in embodiments, the refractometer 110 may be utilized to determine a refractive index of the downhole fluid, which enables identification of the fluid, estimation of fluid properties, and sample cleanup monitoring. For example, the refractometer 110 may be utilized to identify the fluid being recovered by the sampling system 114 to determine whether the near-borehole zone 122 has been purged of drilling mud.

As described above, existing techniques fail to solve problems with downhole fluid analysis. For example, hydrocarbons may absorb the wavelength of light utilized to perform these measurements, thereby leading to erroneous readings. Moreover, flushing fluid at a lens interface may be challenging. Accordingly, systems and methods of the present disclosure may overcome these problems by utilizing a mirror and lens combination that enables both a light source and detector to be located on a same side of the lens in a single pressure housing.

Figure 2:
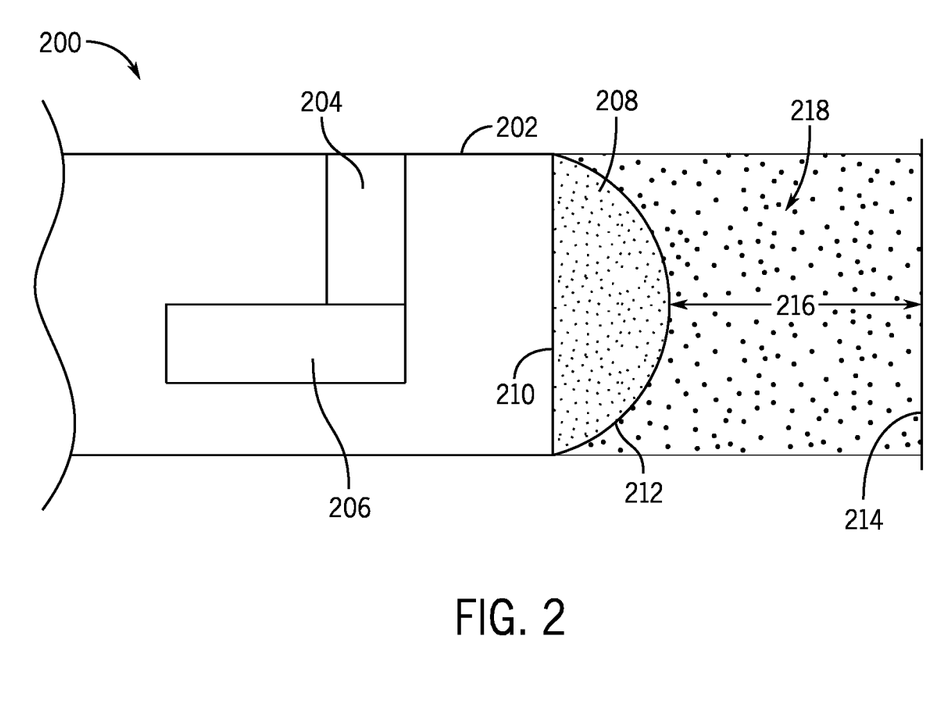
FIG. 2 is a schematic cross-sectional view of an embodiment of an immersed-lens refractometer, in accordance with embodiments of the present disclosure.

FIG. 2 is a schematic diagram of an embodiment of an immersed lens refractometer 200 (e.g., refractometer). The illustrated refractometer 200 includes a pressure housing 202 that houses both a location-sensitive optical detector 204 and a source 206. For example, the location-sensitive optical detector 204 may include a photodiode array, CCD array, or PSD to detect different phases of flow. In various embodiments, the source 206 may emit light toward a lens 208 arranged at an end of the pressure housing 202. The lens 208 may be immersed in a fluid, for example the fluid being evaluated, and may be formed from any reasonable materials, such as sapphire. As will be described below, the illustrated lens 208 is a plano-convex lens that includes a planar side 210 (e.g., flat side, planar end, first end, interior end, interior side, first side) and a convex side 212 (e.g., curved side, curved end, second end, exterior end, exterior side, second side). It should be appreciated that other lens shapes may also be utilized with embodiments of the present disclosure. A small diameter lens of less than 3 mm should be able to withstand the differential pressure between an atmospheric chamber behind it and the formation fluid pressure on the other side. Otherwise, this atmospheric chamber could be filled with a transparent, electrically-nonconducting, pressure-balancing fluid such as a perfluorinated compound (Fomblin, Fluorinert), which is pressurized by a piston or bellows in communication with the formation fluid pressure.

The light source 206 emits the light toward a mirror 214 arranged a distance 216 away from the convex side 212 of the lens 208. In various embodiments, the distance 216 may be measured from an apex or peak location along the curvature of the convex side 212. It should be appreciated that the distance 216 may be particularly selected based on one or more factors of the downhole environment. Moreover, the distance 216 is provided with reference to the convex side 212 for illustrative purposes only and in various embodiments the distance 216 may be based on a distance from the planar side 210, the source 206, the detector 204, or any other reasonable reference point.

The lens 208 directs the light beam toward the mirror 214, as will be described below, and the light beam passes through a fluid 218 positioned between the lens 208 and the mirror 214. For example, in the illustrated embodiment, the convex side 212 is immersed in the fluid 218, along with the mirror 214, while the planar side 210 is within the pressure housing 202 and is isolated from the fluid 218. In operation, light emitted from the source 206 will contact the planar side 210 at a 90 degree angle, thereby preventing bending of the light beam. However, as the light beam contacts the convex side 212, it will bend. Moreover, as the light beam is reflected off of the mirror, it may also bend at various other points, as described below. The beam is eventually received at the detector 204, where different filters or the like may be arranged to determine properties of the fluid 218. For example, filters may block light between various collection points where light being received at those collection points may be correlated to various fluid properties.

Figure 3A:
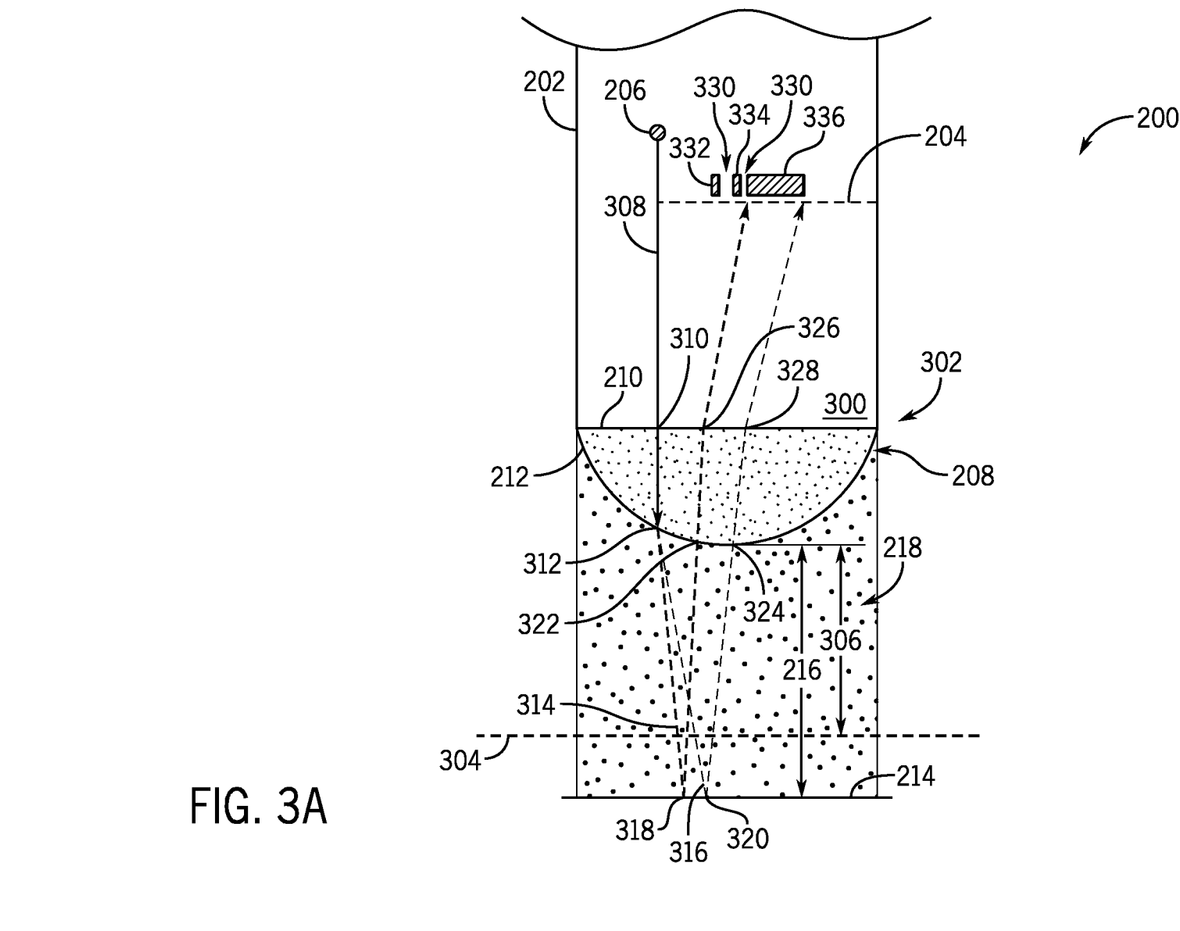
FIG. 3A is a schematic cross-sectional view of an embodiment of an immersed-lens refractometer in a gas, in accordance with embodiments of the present disclosure.
Figure 3B:
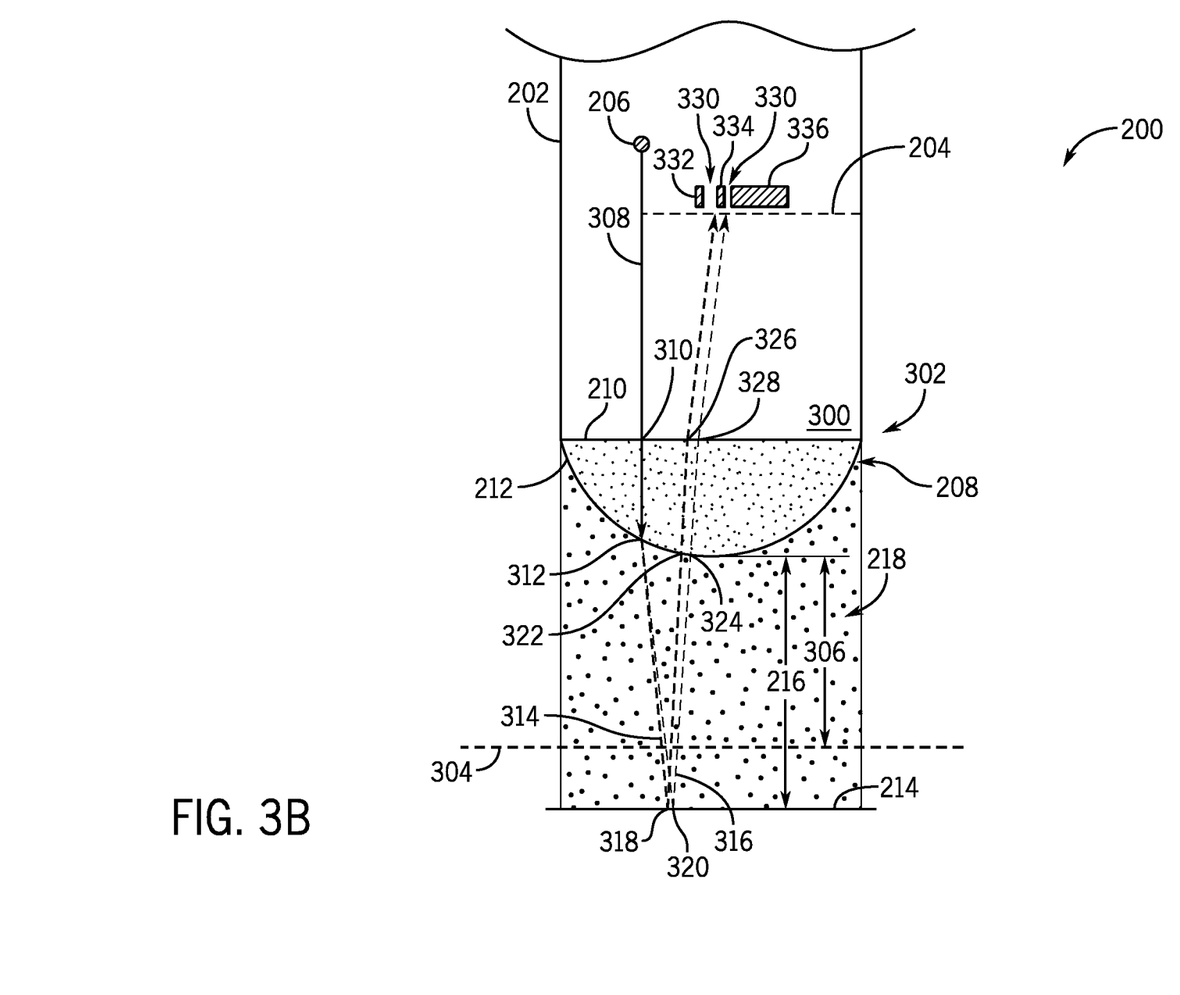
FIG. 3B is a schematic cross-sectional view of an embodiment of an immersed-lens refractometer in water, in accordance with embodiments of the present disclosure.
Figure 3C:
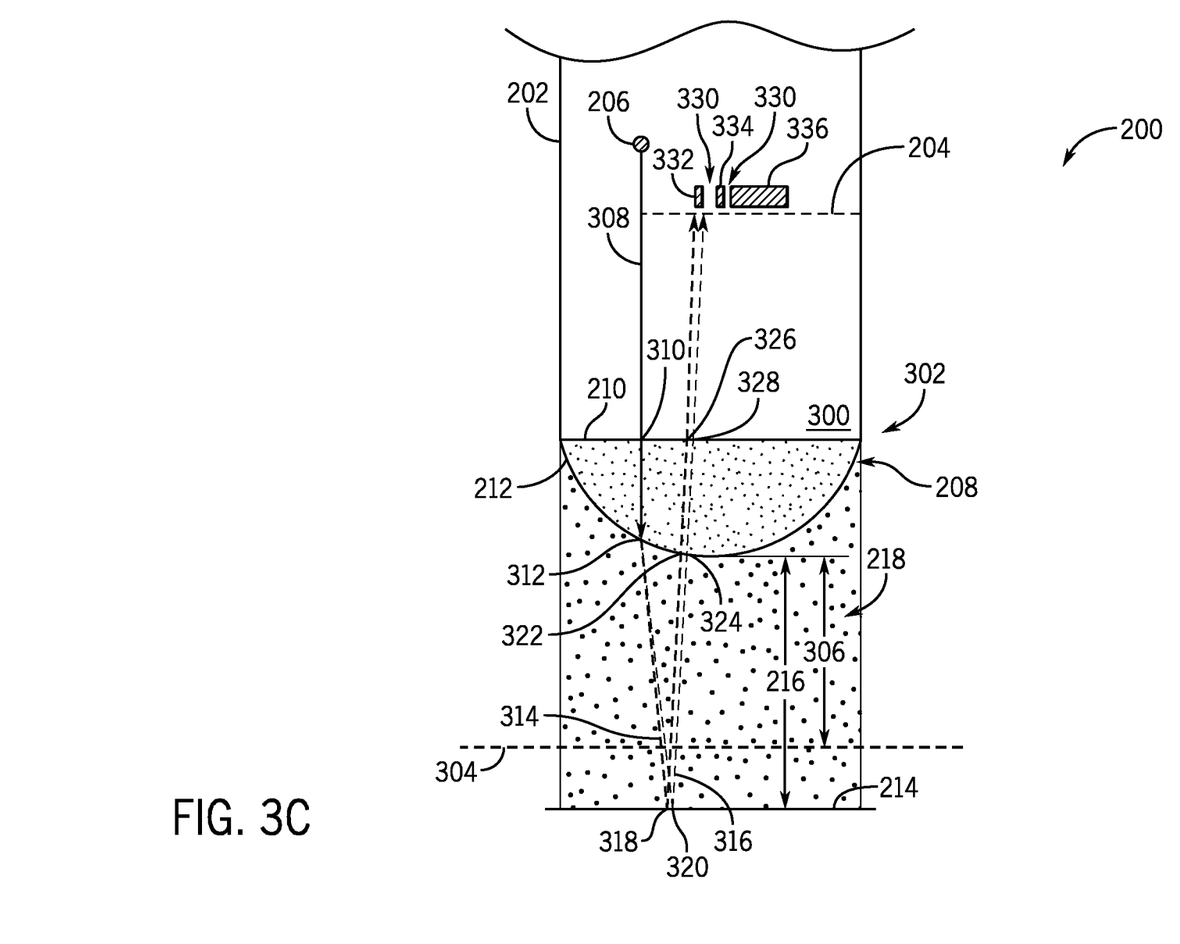
FIG. 3C is a schematic cross-sectional view of an embodiment of an immersed-lens refractometer in oil, in accordance with embodiments of the present disclosure.

FIGS. 3A-3C are schematic diagrams illustrating operation of the refractometer 200 where the fluid 218 corresponds to gas (FIG. 3A), water (FIG. 3B), and hydrocarbon (FIG. 3C). As noted above, the illustrated refractometers 200 include an immersed lens where a single, common pressure housing 202 holds both the light source 206 and the detector 204. Further illustrated is the lens 208 on an end of the pressure housing 202 to direct a light beam from the light source 206 toward the mirror 214. As noted above, the illustrated lens 208 is a plano-convex lens that includes the flat side 210 and the curved side 212. The curved side 212 may be immersed in the fluid 218. As the light beam is directed toward the mirror 214, the beam may bend when it encounters the curved side 212 and/or when it encounters the flat side 210 at a non-perpendicular angle. Due to the different refractive indexes of various fluids that may be detected in downhole environments, different regions may be established with the detector to detect and/or classify properties and/or composition of the downhole fluid.

Embodiments of the present disclosure use an immersed lens to construct a downhole refractometer with no (or substantially no) moving parts. Advantageously, removal of moving parts eliminates potential failure points, such as sliding seals and the like, which may face engineering challenges in downhole environments. Additionally, embodiments of the present disclosure include a single pressure housing that includes both a light source and a detector. In operation, it may be observed that the focal length of a lens, which usually is specified for a lens when it is immersed in air, increases with the refractive index of the fluid in contact with the lens and eventually approaches infinity as the fluid's refractive index approaches the refractive index of the lens. As such, a detector may be constructed that, for example, includes different detection regions based on different phases of flow. For example, a known focal plane for different phases of flow (e.g., gas, water, oil) may be utilized to determine one or more detection regions based on an emergent angle. Accordingly, a location-sensitive optical detector, such as a photodiode array, CCD array, or PSD may be utilized to detect different phases of flow. In embodiments, the lens will be immersed in the fluid and may be formed from sapphire or any other reasonable material.

As noted above, the refractometer 200 includes the pressure housing 202 which positions both the detector 204 and the source 206 within a single, common pressure chamber 300. In various embodiments, the pressure chamber 300 may be maintained at approximately 1 bar of pressure and be filled with air. Positioning these components within a common chamber overcomes problems of current commercial refractometers where various different housings may be utilized to facilitate detection in a downhole environment. The common housing may enable a smaller, more compact device. Moreover, as will be described below, the components may be arranged within the common housing to enable detection without using moving mechanical parts, thereby reducing the likelihood of damage, leaking, or wear in the downhole environment. However, it should be appreciated that the housing 202 may include multiple chambers, for example chambers maintained at different pressures or with different fluids (e.g., nitrogen, air, etc.) and that the illustration of a single, common chamber 300 is not intended to be limiting unless otherwise specifically indicated.

An end 302 of the housing 202 includes the lens 208, which in various embodiments may be a sapphire lens. Sapphire may be selected because of its high refractive index (n=1.75), strength, chemical resistance, and broad wavelength transmission including visible, near-infrared, and mid-infrared. Furthermore, sapphire is used in a variety of downhole applications and has demonstrated sufficient performance. As illustrated, the lens 208 is a plane-convex lens includes the planar side 210 and the convex side 212. It should be appreciated that lenses with different shapes may be utilized in other embodiments and that the lens 208 is for illustrative purposes only.

The illustrated flat side 210 is proximate the chamber 300, and in embodiments may form at least a portion of the chamber 300 or be positioned within the chamber 300, while the curved side 212 may be immersed in the fluid 218. As used herein, a fluid may refer to a gas, liquid, solid, or combination thereof. For example, the fluid may be multi-phase flow. Moreover, various different gas, liquid, or suspended solids components may be included within the fluid. The fluid 218 has a greater refractive index (n) than air. For illustrative purposes only, a focal plane 304 is superimposed within the fluid 218, which would be representative of the focal plane in air, which has a refractive index of approximately 1.000293. However, the refractive index will be different for other fluids.

Further illustrated in FIGS. 3A-3C, and as noted above, is the mirror 214 arranged the distance 216 from the curved side 212 of the lens 208. It should be appreciated that the distance 216 may be particularly selected for design conditions and may further be secured to the pressure housing 202 by various means to maintain the distance 216. By way of example only, a bracket (not illustrated) may be fixed to both the mirror 214 and the pressure housing 202 to secure the mirror 214 into position. In embodiments, the distance 216 may be approximately 2 millimeters. Furthermore, in embodiments, the lens diameter may be approximately 5 millimeters, thereby facilitating a small, compact detector. In the illustrated embodiment, the mirror 214 is arranged farther than the focal plane 304. That is, the distance 216 is larger than a focal plane distance 306.

Turning to FIG. 3A, in operation the light source 206 emits light that forms a beam 308. This beam 308 may also be referred to as an initial beam or first beam, as the beam 308 is emitted directly from the source 206 and travels through the pressure chamber 300 toward the lens 208 arranged at the end 302. The beam 308 contacts the flat side 210 of the lens 208 at a first location 310. Because the beam 308 contacts the flat side 210 at a substantially 90 degree angle, there is no bending. That is, the beam 308 is arranged to be substantially perpendicular to the flat side 210.

The beam 308 encounters the curved side 212 at a second location 312 and bends. As will be appreciated, a beam will bend when encountering a curved surface or a flat surface at a non-perpendicular angle, thereby changing a direction of the beam. In the embodiment illustrated in FIG. 3A, the fluid 218 corresponds to a gas, which has a refractive index between approximately 1.1 and 1.3. Accordingly, for illustrative purposes, two additional beams are shown traveling through the fluid 218. A second beam 314 corresponds to a beam traveling through gas with a refractive index of approximately 1.1, while a third beam 316 corresponds to a beam traveling through gas with a refractive index of approximately 1.3. The second beam 314 is illustrated as a dashed line and the third beam 316 is illustrated with a different dashed pattern to facilitate identification of the beams. As illustrated in FIG. 3A, the different refractive indexes effect how the beams bend, and subsequently, where they contact the mirror 214.

Continuing with the example of FIG. 3A, the second and third beams 314, 316 encounter the mirror 214 at third locations 318, 320, respectively, and are reflected back to the curved side 212. There is a further interaction at the curved side 212 at respective fourth locations 322, 324. Again, due to the interaction with the curved side 212, the beams 314, 316 bend and subsequently encounter the flat side 210 at respective fifth locations 326, 238. Because the beams 314, 316 encounter the flat side 210 at a non-perpendicular angle, there is additional bending.

The beams 314, 316 continue on a path toward the detector 204, which as noted above is arranged within the pressure chamber 300. The beams 314, 316 may interact with the detector 204 and data is collected based on that interaction. For example, fibers may be arranged that record a quantity of light received at the detector 204. As noted above, the detector 204 may include filters 330 and/or regions that particularly correspond to different fluids. For example, the filters 330 are utilized to form the regions that may correspond to different fluid phases. The illustrated detector 204 includes an oil region 332, a water region 334, and a gas region 336. Accordingly, detection within those regions may be utilized to signify and detect the composition of the fluid 218. It should be appreciated that the detector 204 is for illustrate purposes and that, in other embodiments, different detectors may be used. For example, a bundle of optical fibers may be arranged proximate the regions and the brightest fiber bundle (the one that has collected the most light) may provide an indication regarding the composition of the fluid 218.

Similar operation may be illustrated with respect to FIGS. 3B and 3C. As noted above, in various embodiments like reference numerals may be utilized for like components, however, such usage is not intended to limit the scope of the present disclosure. For example, with reference to FIG. 3B, the light source 206 emits light that forms the beam 308 (e.g., first beam) and is directed toward the flat side 210 of the mirror 208. The beam 308 does not bend at the first location 310 because the beam 308 is substantially perpendicular to the flat side 210. The beam 308 continues to interact with the curved side 212 at the second location 312. In this example, the fluid 218 corresponds to water, which has a refractive index of approximately 1.33-1.38. Accordingly, with respect to FIG. 3B, the second beam 314 will correspond to the refractive index of 1.33 and the third beam 316 will correspond to the refractive index of 1.38. It should be appreciated that the illustration of the beams 314, 316 may appear close and/or similar due to the smaller range of water's refractive index when compared to gas and/or oil.

The beams 314, 316 continue to the mirror 214 and interact/reflect at the respective third locations 318, 320. Subsequently, the beams 314, 316 continue to the curved side 212 and bend at the respective fourth locations 322, 324. As the beams 314, 316 interact with the flat side 210 at the fifth locations 326, 328, there is bending because the beams 314, 316 are not substantially perpendicular to the flat side 210. Thereafter, the beams 314, 316 interact with the detector 204, for example, within the water region 334. In this manner, fluid properties 218 may be evaluated as corresponding to water.

As noted above, a similar operation is also illustrated with respect to FIG. 3C, where like reference numerals may be utilized for like components, however, such usage is not intended to limit the scope of the present disclosure. For example, with reference to FIG. 3C, the light source 206 emits light that forms the beam 308 (e.g., first beam) and is directed toward the flat side 210 of the mirror 208. The beam 308 does not bend at the first location 310 because the beam 308 is substantially perpendicular to the flat side 210. The beam 308 continues to interact with the curved side 212 at the second location 312. In this example, the fluid 218 corresponds to oil, which has a refractive index of approximately 1.45-1.55. Accordingly, with respect to FIG. 3C, the second beam 314 will correspond to the refractive index of 1.45 and the third beam 316 will correspond to the refractive index of 1.55.

The beams 314, 316 continue to the mirror 214 and interact/reflect at the respective third locations 318, 320. Subsequently, the beams 314, 316 continue to the curved side 212 and bend at the respective fourth locations 322, 324. As the beams 314, 316 interact with the flat side 210 at the fifth locations 326, 328, there is bending because the beams 314, 316 are not substantially perpendicular to the flat side 210. Thereafter, the beams 314, 316 interact with the detector 204, for example, within the oil region 332. In this manner, fluid properties 218 may be evaluated as corresponding to oil.

Figure 4:
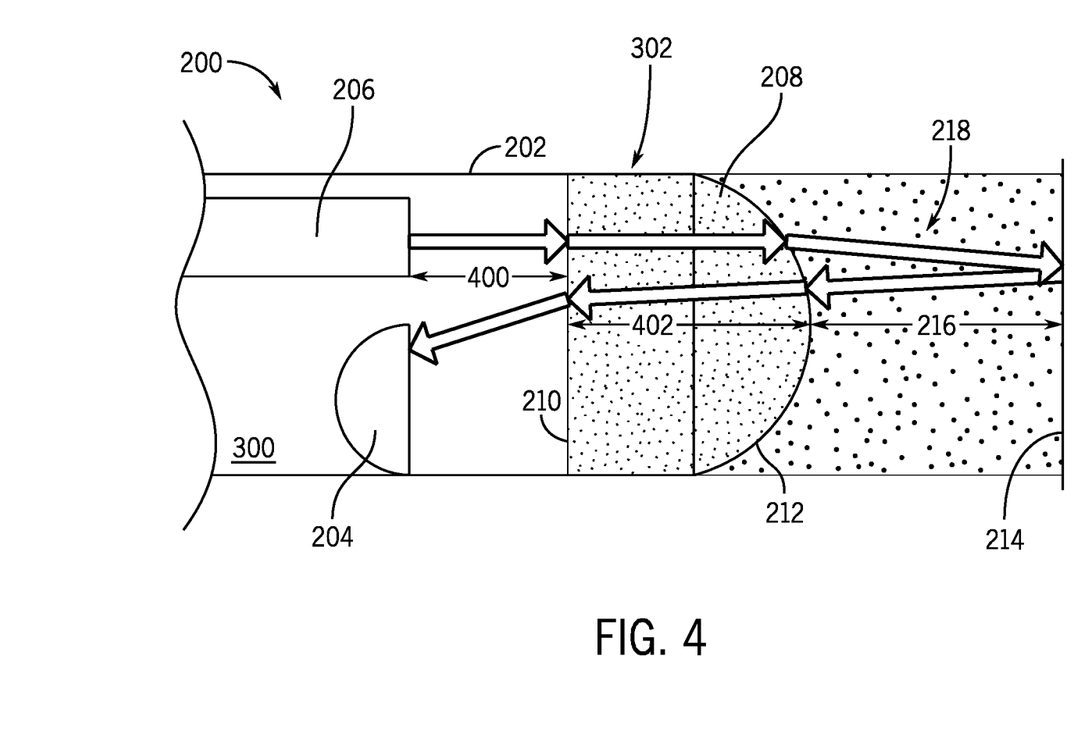
FIG. 4 is a schematic cross-sectional view of an embodiment of an immersed-lens refractometer having a source emitting a beam, in accordance with embodiments of the present disclosure.

FIG. 4 illustrates a schematic cross-sectional view of an embodiment of the refractometer 200. As described above, the refractometer 200 includes the pressure housing 202, which contains both the detector 204 and the light source 206 within a common pressure chamber 300. The lens 208 is arranged at the end 302 of the pressure housing 202, the end 302 is opposite the location of the detector 204 and the light source 206. In the illustrated embodiment, the detector 204 and light source 206 are substantially aligned at a first axial distance 400 from the lens 208 (e.g., from the flat side 210 of the lens 208). It should be appreciated that the first axial distance 400 may be particularly selected based on design conditions.

The illustrated lens 208 has a thickness or second axial distance 402, which is less than the first axial distance 400, in the illustrated embodiment. The second axial distance 402 may be particularly selected based on design conditions, such as anticipated pressures, material used to form the lens 208, and the like. As described above, the illustrated lens includes the flat side 210 and the curved side 212. In operation, the curved side 212 is immersed in the fluid 218, as illustrated in FIGS. 3A-3C.

As described above, the mirror 208 is arranged the distance 216 from the curved side 212 of the lens 208. In operation, the mirror 208 will reflect light from the light source 206 back through the lens 208 to the detector 204. As illustrated in FIG. 4, and described above, the beam 308 is emitted from the light source 206 and interacts with the lens 208. For example, there is an interaction at the flat side 210, which does not bend the beam 308 when the beam 308 interacts with the flat side 210 at a substantially 90 degree angle. However, at the curved side 212, the beam 308 may bend or change direction. Thereafter, as noted above, the mirror 214 may reflect light beams back through the lens 212, where the beams may bend and interact with the lens 212 prior to detection at the detector 204.

In various embodiments, the geometry of the system, as well as the materials, may be particularly selected. For example, computer methods such as simulation code via Zemax OpticStudio® may be utilized to simulate the optical configuration described herein. In embodiments, the source may be a 1310 nm laser diode, however other light sources 206 may also be used. It should be appreciated that a variety of variations may be incorporated into embodiments of the present disclosure. For example, various fluids may be detected or utilized for modeling, such as water, methane (8, 12 and 16 kpsi), ethane (4, 8, 12 and 16 kpsi), propane (8, 12 and 16 kpsi) and butane (8, 12 and 16 kpsi). Furthermore, as noted, dimensions of various features of the present disclosure may be particularly selected based on operating conditions and the like. For example, a distance from the light source to the lens may be in a range of 0-10 mm. A distance from the detector to the lens may be in a range of 0-10 mm. A distance from the convex side of the lens to the mirror may be in a range of 1-3 mm. A lens thickness may vary. A radius of curvature of the convex side of the lens may be in a range of 0 (plane) to 6 mm. A radius of curvature of the mirror may be in a range of 0 (plane) to 6 mm. Furthermore, while embodiments may illustrate a mirror that has substantially zero tilt relative to an axis of the pressure housing, in other embodiments the mirror may be tilted. Furthermore, as described above, lens material may vary and may include material such as sapphire, germanium, silicon, and the like. Adjustment of the various properties may be performed while considering criteria such as ability to transmit the light through the different fluids, dispersion of the light by the lens on the way back to the detector, dimensions of the overall system, and other operational aspects.

In various embodiments, light collection may be improved by using a curved mirror. As for the lens material, simulation shows that sapphire performs better than germanium and silicon in terms of transmission, light focusing and reduced light loss; however, germanium and silicon would allow for more compact systems. As a result, each of these materials, as examples only, may be utilized in various embodiments.

Simulations show that a concave mirror (instead of a flat one) helps with the focusing of the light back through the lens and onto the detector. The focal length of a concave mirror is half of its radius of curvature whereas the focal length of a lens depends not only on its radii of curvature but on the lens' index of refraction and the refractive index of the medium in which is it immersed. Table 1, below, shows that the favorable results for light intensity at the detector occur when the mirror's focal length is close to the focal length of the lens in the fluid.

TABLE 1

| Lens | Lens Thickness (mm) | R1 (mm) | R2 (mm) | $n_{lens}$ | $n_{fluid}$ | $n_{image}$ (air) | Focal Length |
|---|---|---|---|---|---|---|---|
| Sapphire | 1 | 0 | −3 | 1.768 | 0004 to 1.33 | 1.0003 | 3.9078 |
| Germanium | 1 | 0 | −3 | 4.003 | 0004 to 1.33 | 1.0003 | 0.9991 |
| Silicon | 1 | 0 | −3 | 3.422 | 0004 to 1.33 | 1.0003 | 1.2388 |
| Mirror | NA | −6 | NA | | | | 3 |

Figure 5:
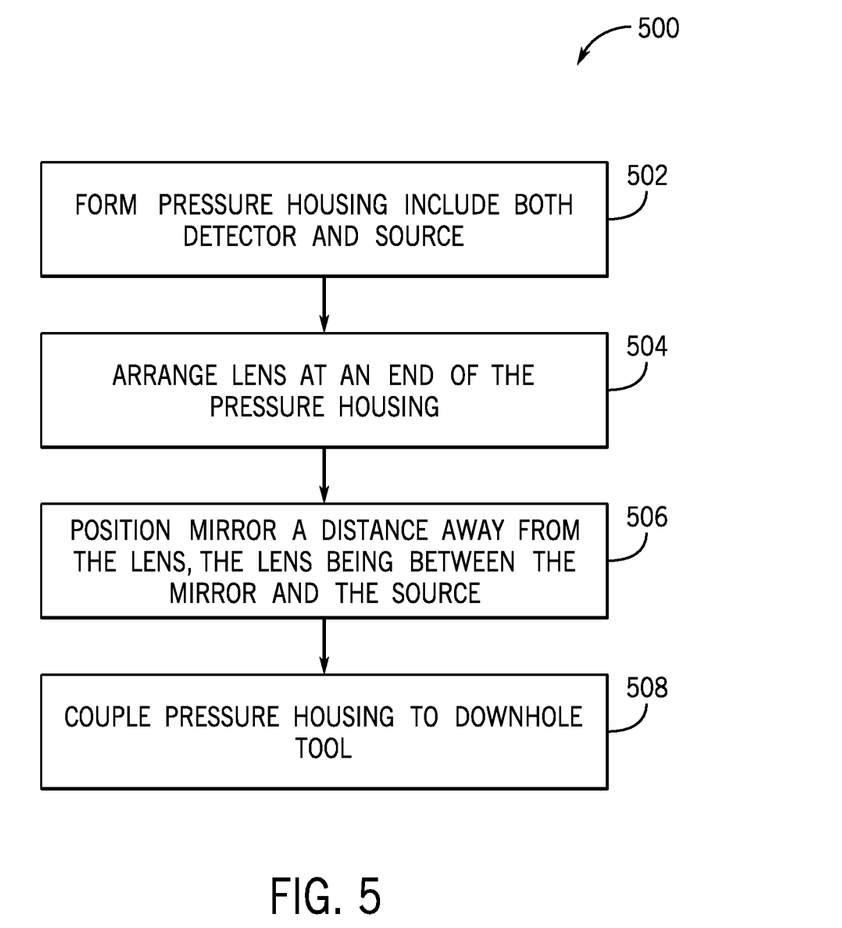
FIG. 5 is a flow chart of an embodiment of a method for forming an immersed-lens refractometer, in accordance with embodiments of the present disclosure.

FIG. 5 is a flow chart of an embodiment of a method 500 for forming a refractometer. It should be appreciated that for this method, and all methods discussed herein, that there may be more or fewer steps, and that the steps may be performed in a different order, or in parallel, unless otherwise specifically stated. This example begins with forming a pressure housing that includes both a light source and a detector 502. In various embodiments, the light source and the detector are aligned within the detector such that they are arranged an equal distance from an end of the pressure housing and/or another component in the pressure housing. The pressure housing may include a chamber that maintains both the light source and the detector at a certain temperature and/or pressure and protects the components from a wellbore environment. In various embodiments, the pressure housing is filled with air.

A lens is arranged at an end of the pressure housing 504. For example, a plano-convex lens may be positioned at the end such that a flat end of the lens is proximate the pressure chamber (e.g., closer to the detector and/or light source) than a curved end. In various embodiments, the curved end will be exposed to wellbore fluids while the flat end is not. In embodiments, a mirror is arranged a distance from the lens 506. For example, the mirror may be coupled to the pressure housing and positioned a predetermined distance from the lens. In various embodiments, the mirror is substantially flat and perpendicular to an axis of the pressure housing, however, in various embodiments the mirror may be curved and/or arranged at an acute or obtuse angle with respect to the axis of the pressure housing. The arrangement of the pressure housing and mirror is then coupled to a downhole tool 508, which may be deployed during wellbore operations. In this manner, data may be collected from the downhole environment.

Figure 6:
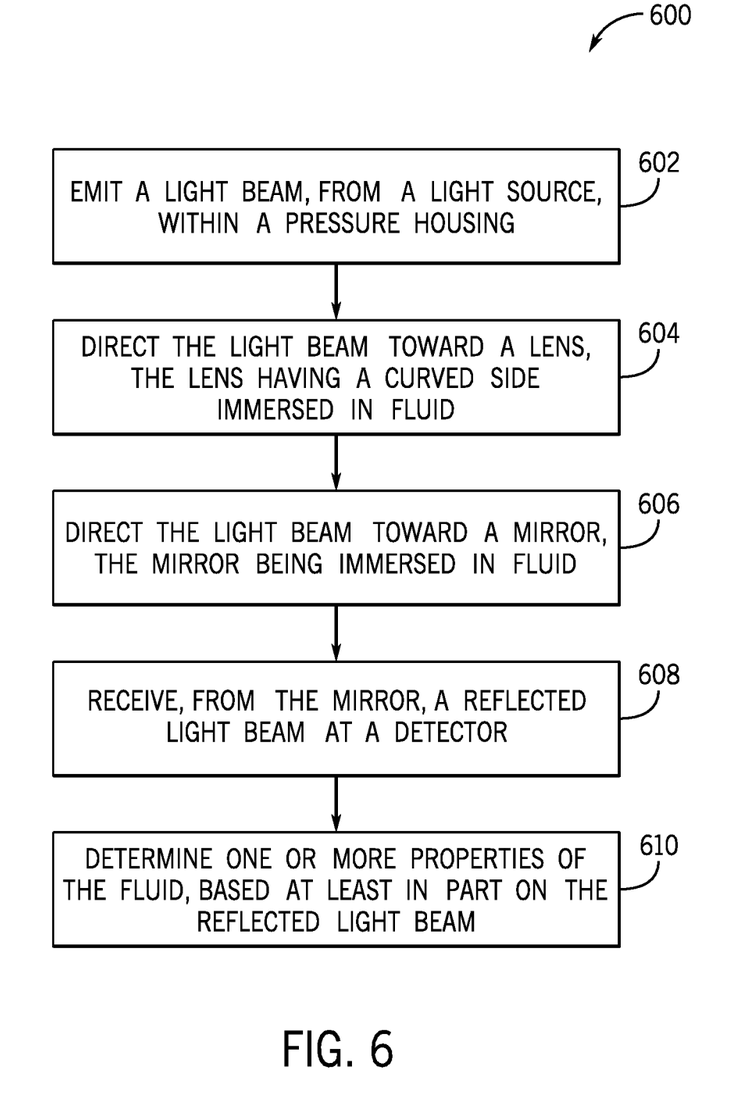
FIG. 6 is a flow chart of an embodiment of a method for determining one or more fluid properties, in accordance with embodiments of the present disclosure.

FIG. 6 is a flow chart of an embodiment of a method 600 for determining one or more properties of a wellbore fluid. This example begins by emitting a light beam, for example, from a light source arranged within a pressure housing positioned in a downhole environment 602. The light beam is directed toward a lens 604, which may be a plano-convex lens that includes a flat side and a curved side. In various embodiments, the lens is arranged such that the curved side is immersed within the wellbore fluid while the flat side is positioned proximate the pressure housing.

The light beam is further directed toward a mirror 606, which may also be immersed in the fluid, which reflects the light back toward the pressure housing. The reflected light beam is received at a detector 608. Information from the detector is then utilized to determine one or more properties of the fluid 610. For example, the detector may determine a composition of the fluid, a phase of the fluid, or the like based on an analysis of the data collected by a processor executing instructions stored on a memory. The processor and memory may be a downhole or uphole system that receives the data, for example via one or more communication systems, and then analyses the data based on machine-readable instructions executed by the processor.

Although the technology herein has been described with reference to particular embodiments, it is to be understood that these embodiments are merely illustrative of the principles and applications of the present technology. It is therefore to be understood that numerous modifications may be made to the illustrative embodiments and that other arrangements may be devised without departing from the spirit and scope of the present technology as defined by the appended claims.

The invention claimed is:

1. An apparatus for detecting one or more properties of a downhole fluid, comprising:
   a housing;
   a refractometer comprising a location-sensitive optical detector, arranged within a chamber formed by the housing, to determine a refractive index of a fluid;
   a light source, arranged within the chamber;
   a lens, positioned at an end of the housing to form a barrier between the chamber and the fluid, external to the housing, such that the lens contacts the fluid; and
   a mirror, arranged outside the housing;
   wherein the location-sensitive optical detector is positioned to receive a beam, generated by the light source, that is bent after interaction with at least one of the lens, the fluid, or the mirror, such that an angle of the beam interacting with the location-sensitive optical detector is indicative of a phase of the fluid.

2. The system of claim 1, wherein the location-sensitive optical detector includes a photodiode array, a Charge-Coupled Device (CCD) array, a Position Sensitive Detector (CCD), or a combination thereof.

3. The system of claim 1, wherein the lens comprises:
   a flat side; and
   a curved side;

wherein the flat side is positioned proximate the chamber to position the flat side closer to the light source than the curved side.

4. The system of claim 3, wherein the beam emitted from the light source contacts the flat side without bending, bends a first time at the curved side, reflects off the mirror, bends a second time at the curved side, and bends a third time at the flat side before being received at the location-sensitive optical detector.

5. The system of claim 1, wherein the refractometer further comprises:
   a plurality of filters separating light collection points of the location-sensitive optical detector.

\* \* \* \* \*